(12) United States Patent
Suda et al.

(10) Patent No.: US 7,674,782 B2
(45) Date of Patent: Mar. 9, 2010

(54) PHOSPHORYLCHOLINE GROUP-CONTAINING COMPOUND AND METHOD FOR PRODUCING SAME

(75) Inventors: Yukimitsu Suda, Yokohama (JP); Kazuyuki Miyazawa, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 49 days.

(21) Appl. No.: 11/664,670

(22) PCT Filed: Nov. 28, 2005

(86) PCT No.: PCT/JP2005/021795

§ 371 (c)(1),
(2), (4) Date: Apr. 4, 2007

(87) PCT Pub. No.: WO2006/057384

PCT Pub. Date: Jan. 6, 2006

(65) Prior Publication Data

US 2008/0113942 A1    May 15, 2008

(30) Foreign Application Priority Data

Nov. 29, 2004   (JP) ............................. 2004-343375
Nov. 28, 2005   (JP) ............................. 2005-341934

(51) Int. Cl.
*A61K 31/685*   (2006.01)
*C07F 9/02*      (2006.01)
*C08F 30/02*    (2006.01)

(52) U.S. Cl. ............................. 514/78; 564/78; 526/277

(58) Field of Classification Search ................... 514/78, 514/75; 510/433; 554/78; 562/11; 525/328.8, 525/328.2, 329.7; 526/274, 277

See application file for complete search history.

(56) References Cited

FOREIGN PATENT DOCUMENTS

| EP | 1 690 867 A1 | 8/2006 |
| EP | 1 750 159 A1 | 2/2007 |
| JP | 2004-175676 | 6/2004 |
| WO | WO 91/13639 | 9/1991 |

OTHER PUBLICATIONS

Berge, S.M., et al. Pharmaceutical Salts, 1977, Journal of Pharmaceutical Sciences, vol. 66, No. 1, pp. 1-19.*

Kazuhiko Ishihara, et al., "Preparation of Phospholipid Polymers and Their Properties as Polymer Hydrogel Membranes", Polymer Journal, vol. 22, No. 5, pp. 355-360 (1990).

G. Rao, et al., "Irreversible Inhibition of a Monoclonal Antibody by a Nitrophenyl Ester", Journal of Protein Chemistry, vol. 10, No. 1, pp. 117-122 (1991).

* cited by examiner

*Primary Examiner*—Porfirio Nazario-Gonzalez
*Assistant Examiner*—Yate' K Cutliff
(74) *Attorney, Agent, or Firm*—Townsend & Banta

(57) ABSTRACT

The present invention is a phosphorylcholine-containing chemical compound represented by the following formula (1) or (2).

$$(CH_3)_3N^+CH_2CH_2PO_4^-CH_2COOH \quad (1)$$

$$(CH_3)_3N^+CH_2CH_2PO_4^-CH_2COONa \quad (2)$$

The object of the present invention is to provide a new phosphorylcholine-containing compound that is useful as a surface treatment agent or a source material of a surface treatment agent. Another object is to provide a manufacturing method that has a high industrial utility value.

3 Claims, 3 Drawing Sheets

PHOSPHORYLCHOLINE GROUP-CONTAINING COMPOUND AND METHOD FOR PRODUCING SAME

TECHNICAL FIELD

The present invention relates to a phosphorylcholine group-containing chemical compound and a method for manufacturing thereof.

The phosphorylcholine group-containing chemical compound of the present invention is a useful compound as a surface treatment agent or a source material of a surface treatment agent for materials such as plastics, metal, and glass.

The surface modifier consisting of the compound of the present invention can give biocompatibility, moisture retaining properties, hydrophilicity, and other various useful functions to objects.

BACKGROUND ART

Phosphorylcholine group-containing chemical compounds are used as surface treatment agents to improve biocompatibility and such. For example, in Patent document 1 they are used as surface treatment agents for diagnostic equipment and contact lenses for the purpose of decreasing the deposition of proteins and cells.

In Patent document 1, the phosphorylcholine group-containing chemical compound used as a surface treatment agent is the compound of formula (I) in claim 1 of the patent. This compound is obtained from a reaction of the carboxyl phosphorylcholine derivative shown in formula (V) in the right lower column of page 5. That is, an appropriate compound chosen from the carboxyl phosphorylcholine derivatives of general formula (V) is used.

The appropriate carboxyl phosphorylcholine derivatives represented by formula (V) are compounds having chemical structures that are considered usable as a source material compound to manufacture the compound of surface treatment agent formula (I) and they are shown in the form of a general formula. In the right lower column of page 6 of the document, the following formula (4) is shown as the compound having the simplest structure that meets this general formula. From this it can be understood that the compound having the simplest structure that meets formula (V) is the most useful. This reaction formula (6) describes the compound of formula (4) as an ideal compound conceivable for use in a reaction to manufacture the compound of formula (I), a surface treatment agent; however, this is not an existing compound actually synthesized in Patent document 1: this is not a prior art compound actually synthesized.

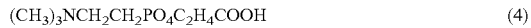

$(CH_3)_3NCH_2CH_2PO_4C_2H_4COOH$ \hfill (4)

For the carboxyl phosphorylcholine having a simple structure that is a prior art compound included in general formula (V), the compound of the following formula (5) is reported to have been bought from Molecular Probe Inc. (Non-Patent document 1). However, Non-Patent document 1 does not mention specific synthesis examples, and no corresponding chemical compound has been found on Molecular Probe's website.

$(CH_3)_3NCH_2CH_2PO_4C_5H_{10}COOH$ \hfill (5)

However, the compound of formula (5) is not sufficient for endowing these materials with maximum biocompatibility because of the spacer ($C_6H_{10}$ portion) that binds the phosphorylcholine group portion, which is involved in biocompatibility, and the material to be treated.

With regards to methods for manufacturing phosphorylcholine compounds, several synthesis examples have been proposed (Patent documents 2-4, Non-patent documents 2).

However, these methods use phosphorus oxychloride for the starting substance and therefore have a shortcoming in that they are cumbersome methods.

For example, the reaction must be carried out under strict moisture-free conditions. Therefore, moisture in the reaction atmosphere must be removed as well.

Also, the purification process for the target phosphorylcholine compound is cumbersome and its purification is quite difficult. The reaction yield is low as well.

Furthermore, an organic solvent is used for the reaction solvent, which means purification of the reaction solvent (moisture removal) has to be carried out strictly and there are environmental problems due to the use of the organic solvent.

As described thus far, conventional methods to manufacture phosphorylcholine compounds that use phosphorus oxychloride as the starting substance have many problems as an industrial manufacturing method.

Patent Document 1: Japanese Patent Laid-Open H5-505121 bulletin

Patent Document 2: Japanese Patent Laid-Open S63-222183 bulletin

Patent Document 3: Japanese Patent Laid-Open H7-10892 bulletin

Patent Document 4: U.S. Pat. No. 5,648,442 bulletin

Non-patent document 1: Journal of Protein Chemistry, 117 (10) 1 1991

Non-patent document 2: Polymer Journal, vol. 22 355-360 (1990)

DISCLOSURE OF INVENTION

[Problem That the Present Invention Aims to Solve]

As described above, among the compounds included in general formula (V), those having the simplest structures are very useful.

In view of the problems described above, the present invention provides a newly synthesized carboxyl phosphorylcholine; it provides the most ideal compound that has a structure even simpler than the compound of formula (4), which is the ideal compound among carboxyl phosphorylcholine derivatives of formula (V) in said Patent document 1.

The method for manufacturing this compound is not a conventional method that uses phosphorus oxychloride as the starting substance; it is a reaction in a water based solvent (a reaction that does not require moisture-free conditions) using glycerophosphorylcholine as the starting substance, thus brilliantly solving many problems that come with the conventional method.

Also, the chemical compound of the present invention is not only the source compound for manufacturing the compound of surface treatment agent formula (I) of Patent document 1 but also a compound that has been confirmed to be useful as a surface treatment agent by itself. The chemical compound of the present invention is used as a surface treatment agent; it allows the phosphorylcholine group portion, which gives biocompatibility, to reside closest to the material surface (the spacer is methylene, which is C1) and therefore various surface modification functions of phosphorylcholine groups including biocompatibility can be maximally manifested on the material surface.

[Means to solve the Problem]

That is, the present invention provides a phosphorylcholine group-containing chemical compound represented by the following general formula (1) or (2).

$$(CH_3)_3N^+CH_2CH_2PO_4^-CH_2COOH \quad (1)$$

$$(CH_3)_3N^+CH_2CH_2PO_4^-CH_2COONa \quad (2)$$

Also, the present invention provides a method for manufacturing the phosphorylcholine group-containing chemical compound represented by the following formula (1) or (3) in which glycerophosphorylcholine, periodic acid and/or periodate in the amount of 3 or more equivalents of that of glycerophosphorylcholine, and a trivalent ruthenium compound are reacted in an aqueous solution.

$$(CH_3)_3N^+CH_2CH_2PO_4^-CH_2COOH \quad (1)$$

$$((CH_3)_3N+CH_2CH_2PO_4^-CH_2COO-)_nM^{n+} \quad (3)$$

M denotes a cation, and n denotes the valency of the cation.

Furthermore, the present invention provides a method for manufacturing the phosphorylcholine group-containing chemical compound represented by the following formula (1) or (3) in which glycerophosphorylcholine, periodic acid and/or periodate in the amount of 3 or more equivalents of that of glycerophosphorylcholine, and a divalent ruthenium compound are reacted in an aqueous solution.

$$(CH_3)_3N^+CH_2CH_2PO_4^-CH_2COOH \quad (1)$$

$$((CH_3)_3N^+CH_2CH_2PO_4^-CH_2COO^-)_nM^{n+} \quad (3)$$

M denotes a cation, and n denotes the valency of the cation.

Also, the present invention provides a method for manufacturing the phosphorylcholine group-containing chemical compound represented by the following formula (1) or (3) in which glycerophosphorylcholine, and permanganic acid and/or permanganate are reacted in an aqueous solution.

$$(CH_3)_3N^+CH_2CH_2PO_4^-CH_2COOH \quad (1)$$

$$((CH_3)_3N^+CH_2CH_2PO_4^-CH_2COO^-)_nM^{n+} \quad (3)$$

M denotes a cation, and n denotes the valency of the cation.

Furthermore, the present invention provides a surface treatment agent composed of a phosphorylcholine group-containing chemical compound represented by the following general formula (1) or (3).

$$(CH_3)_3N^+CH_2CH_2PO_4^-CH_2COOH \quad (1)$$

$$((CH_3)_3N^+CH_2CH_2PO_4^-CH_2COO^-)_nM^{n+} \quad (3)$$

M denotes a cation, and n denotes the valency of the cation.

EFFECTS OF THE INVENTION

The new chemical compound of the present invention is a carboxyl phosphorylcholine that has the simplest structure and it is a highly useful compound. It is on its own used as a surface treatment agent; it allows the phosphorylcholine group portion, which gives biocompatibility, to reside closest to the material surface (the spacer is methylene, which is C1) and therefore surface modification functions of phosphorylcholine groups including biocompatibility is maximally manifested on the material surface.

It is also possible to obtain a new surface treatment agent by reacting the new chemical compound of the present invention with a compound having a useful reactive group other than a carboxyl group. For example, a silane coupler having a phosphorylcholine group can be easily obtained by reacting the new chemical compound of the present invention with aminopropyltrimethoxysilane, i.e. it is useful for a source material (intermediate) for a surface treatment agent as well.

The manufacturing method of the present invention is a simple manufacturing method using glycerophosphorylcholine for the starting substance. Glycerophosphorylcholine comes from naturally existing raw materials such as lecithin and can be obtained commercially at a low cost and in large quantities.

It can be manufactured in a water based solvent. The reaction proceeds quantitatively and the yield is very high. Furthermore, the purification process is simple.

BEST MODE FOR CARRYING OUT THE INVENTION

Figure 1:
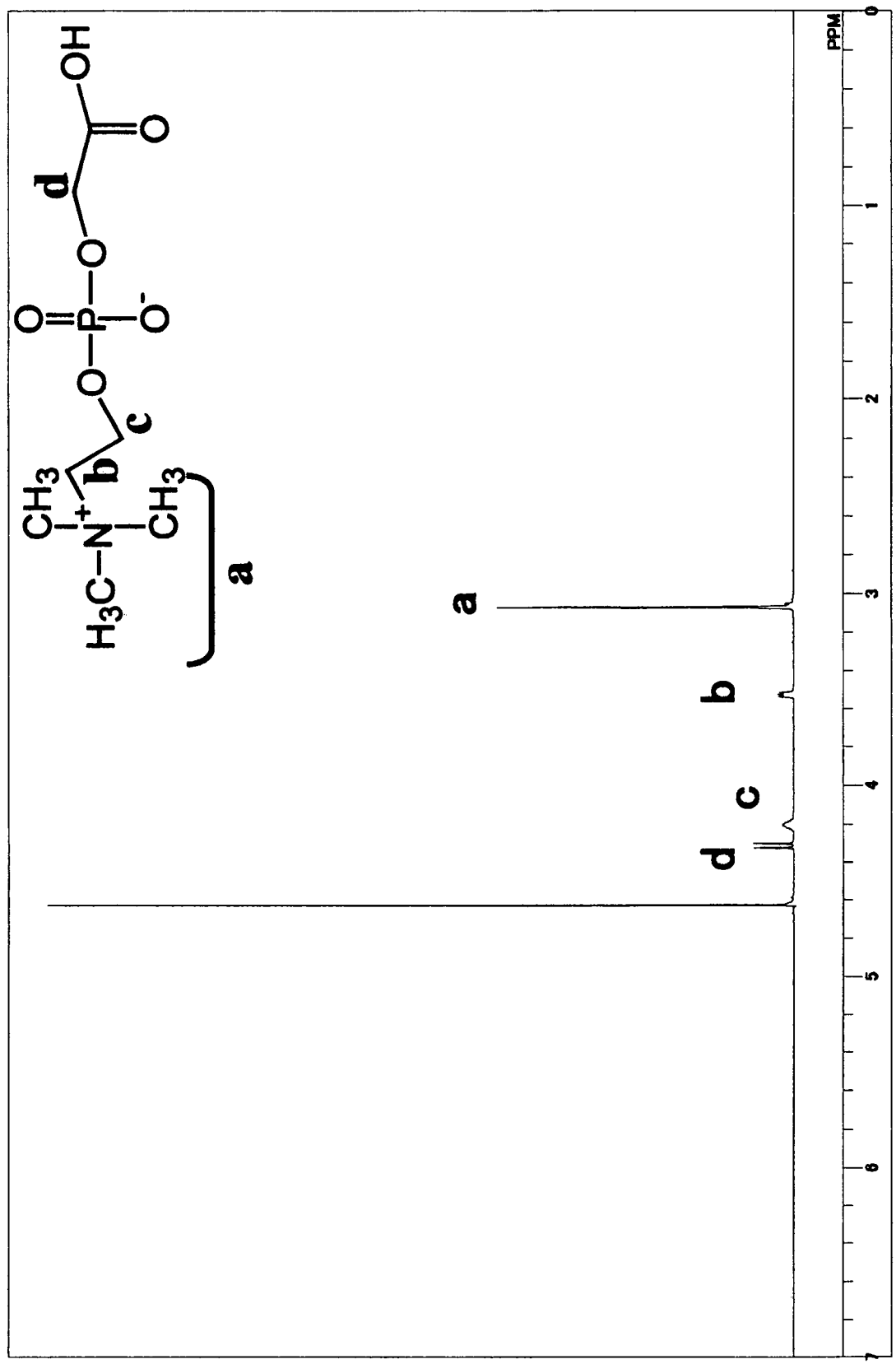
FIG. 1 is a 1H-NMR spectrum of the chemical compound of the present invention prepared in Example.

The structures of the new chemical compounds (1) and (2) of the present invention are as follows.

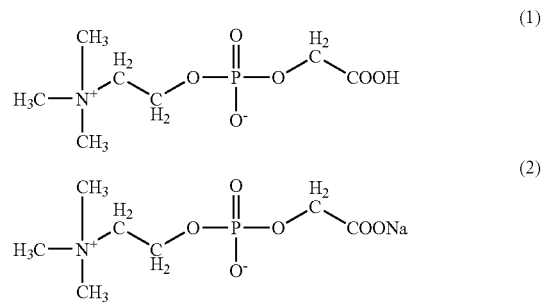

This compound can be prepared by stirring and reacting periodic acid and/or periodate in the amount of 3 equivalents or more of that of glycerophosphorylcholine, and a trivalent and/or divalent ruthenium compound in an aqueous solution (the reaction rate increases by addition of acetonitrile).

Commercial products can be used for the glycerophosphorylcholine, periodic acid, periodate, trivalent ruthenium compound, divalent ruthenium compound, and acetonitrile. Examples of periodic acid include orthoperiodic acid, metaperiodic acid, and hydrates thereof. Examples of periodate include sodium periodate, potassium periodate, calcium periodate, and hydrates thereof. Examples of trivalent ruthenium compounds include ruthenium trichloride, ruthenium tribromide, tris (acetylacetonato) ruthenium, and hydrates thereof. Examples of divalent ruthenium compounds include hexaammine ruthenium dichloride, potassium hexacyanoruthenate, and hydrates thereof.

When periodate is used, the compound of the following formula (1) or (3) can be prepared.

In formula (3), M denotes the cation corresponding to the periodate, and n denotes the valency of the cation. Representative cations are alkali metal ions, alkali earth metal ions, and ammonium ion.

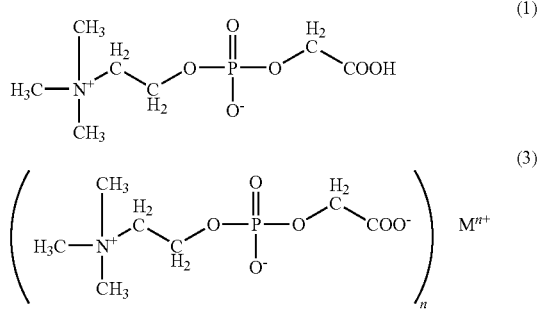

M denotes a cation, and n denotes the valency of the cation.

The periodic acid and/or periodate is characteristically used in the amount of 3 equivalents or more of the glycerophosphorylcholine. Preferably 4 equivalents or more should be used. Four equivalents or more will give a yield of almost 100%. If it is 2 equivalents, then the yield is low even if the reaction time is long, which is not suitable for practical use.

The necessary amount of the trivalent and/or divalent ruthenium compound is only a catalytic amount (approximately 0.02 mole %)

The reaction solvent is water. Organic solvents are not used, which is environmentally significant for an industrial manufacturing method. The addition of acetonitrile will increase the reaction rate. The mixing ratio of water and acetonitrile is not limited in particular. An organic solvent can be freely added to the water.

The reaction proceeds sufficiently at room temperature.

The reaction time is not limited in particular; approximately 2 hours is sufficient to complete the reaction with a virtually 100% yield.

After completion of the reaction, the solvent is removed. The compound of the present invention can be extracted from the remaining solid by using methanol. Methanol is then removed to obtain the compound of the above formula (1) or (3). When sodium periodate is used, the compound of formula (1) or (2) of the present invention is obtained.

The obtained compound can be recrystallized from a methanol solution at rest or by adding acetonitrile to obtain a higher purity target compound.

The compound of formula (1) is 2[[[(carboxymethyl)oxy]hydroxyphosphinyl]oxy]-N,N,N-trimethyl-ethanaminium, and the compound of formula (2) is its sodium salt.

The compounds of formula (1) and (2) can be separated by means of a prior art method. For example, the compound of formula (1) alone can be obtained by treating a mixture of formulas (1) and (2) with hydrochloric acid and such. Also, the mixture can be turned into the compound of formula (2) alone by neutralizing it with sodium hydroxide and such.

Even when formula (1) and formula (2) are mixed together, they can be used as a surface treatment agent or as the source material to manufacture other compounds (such as surface treatment agents).

In addition to the methods described above, the compound of formula (1) can be obtained by an oxidative cleave reaction of the proximal diol by using, as a catalyst, lead tetraacetate or permanganic acid supported in silica gel, tungsten, iron, vanadium, or molybdenum.

The compound of formula (1) or (3) can be prepared by stirring and reacting glycerophosphorylcholine and permanganic acid and/or permanganate in an aqueous solution. Examples of permanganate include potassium permanganate, sodium permanganate, and hydrates thereof.

The compound of the present invention can give biocompatibility, moisture retaining properties, hydrophilicity, and other various useful functions to objects. It is a very useful compound as a surface treatment agent or a source material for a surface treatment agent for various materials such as plastic, metal, and glass.

EXAMPLES

The invention is described in specific detail through Examples.

"Materials Used"

In the following preparation methods, the following commercially available products were used as source materials.

Glycerophosphorylcholine (from Chemi)

Acetonitrile (highest quality reagent from Wako Pure Chemical Industries, ltd.)

Sodium periodate (highest quality reagent from Wako Pure Chemical Industries, ltd.)

Ruthenium n-hydrate (highest quality reagent from Wako Pure Chemical Industries, ltd.)

Hexaammine ruthenium dichloride (from Aldrich)

Potassium permanganate (highest quality reagent from Wako Pure Chemical Industries, ltd.)

"Manufacturing Method 1: A Manufacturing Method Using a Trivalent Ruthenium Compound (Claim 2)"

5 g (19.4 mmol) of glycerophosphorylcholine, 17 g (79.7 mmol, 4.1 eq) of sodium periodate, 81 mg (0.39 mmol, 0.02 mol %) of ruthenium trichloride n-hydrate, 70 g of ion-exchanged water, and 30 g of acetonitrile were added into a 200 ml flask. After stirring for two hours at room temperature, filtering was carried out and the solvent was removed from the filtrate. Methanol was used to extract the target compound from the obtained solid product; methanol was then removed to obtain the target compound. The reaction yield was almost 100%.

Figure 2:
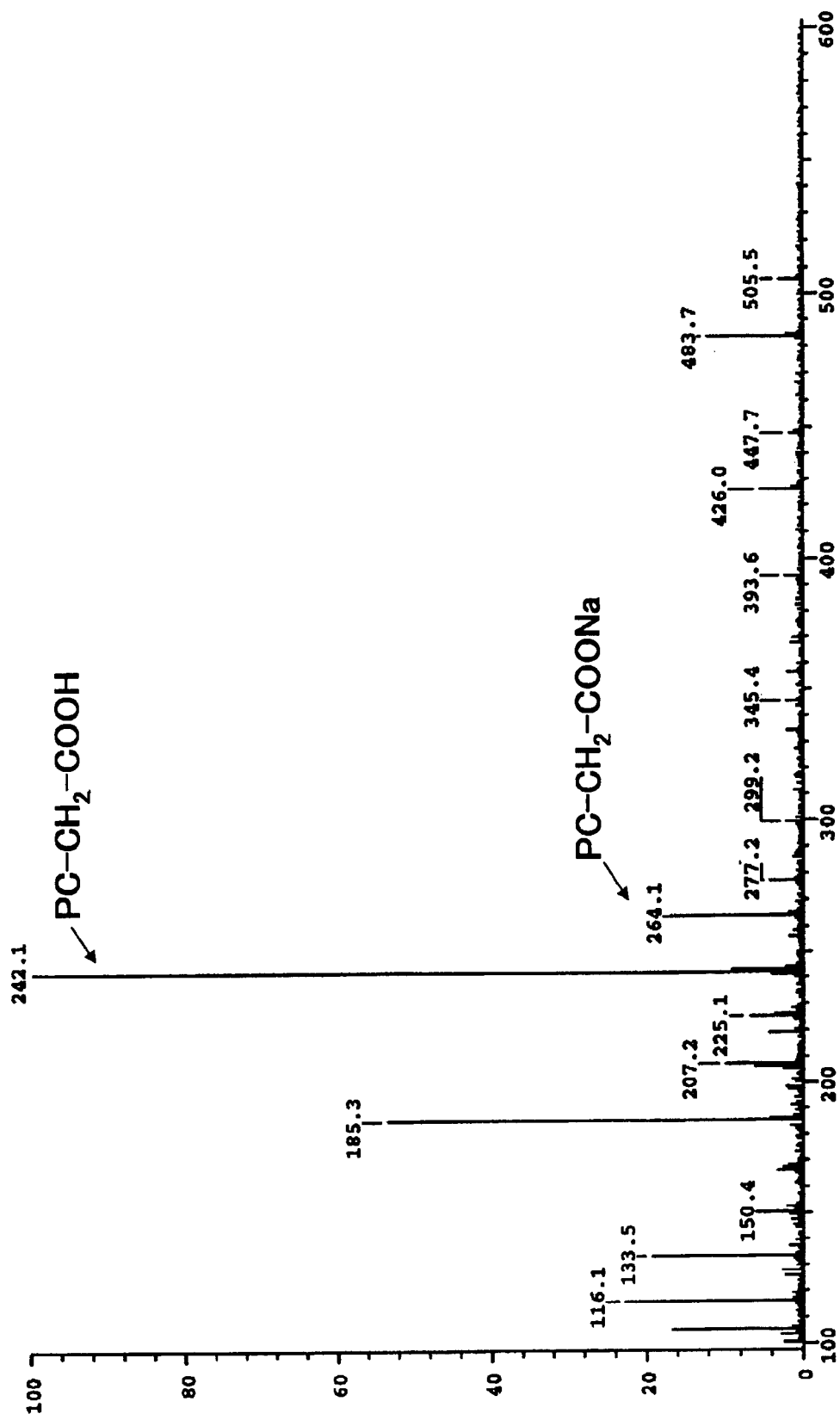
FIG. 2 is a mass spectrum of the chemical compound of the present invention prepared in Example.
Figure 3:
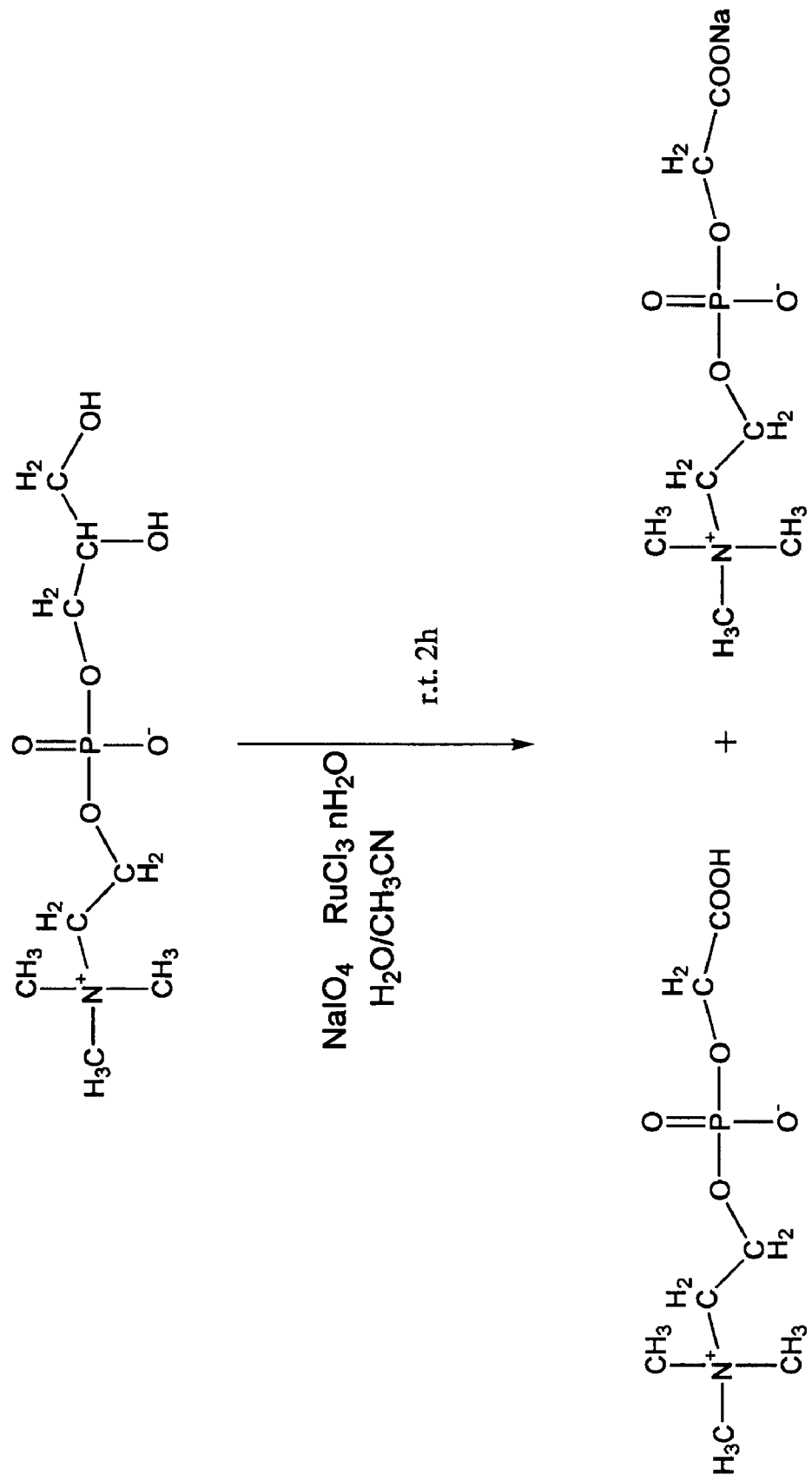
FIG. 3 shows the reaction formula of Manufacturing method 1.

FIG. 1 shows the $^1$H NMR spectrum and FIG. 2 shows a mass spectrum. They indicate that the target compound of formula (1) or formula (2) was obtained. The reaction formula is shown in FIG. 3.

"Manufacturing Method 2: A Manufacturing Method Using a Divalent Ruthenium Compound (Claim 3)"

5 g (19.4 mmol) of glycerophosphorylcholine, 17 g (79.7 mmol, 4.1 eq) of sodium periodate, 107 mg (0.39 mmol, 0.02 mol %) of hexaammine ruthenium dichloride, 70 g of ion-exchanged water, and 30 g of acetonitrile were added into a 200 ml flask. After stirring for two hours at room temperature, filtering was carried out and the solvent was removed from the filtrate. Methanol was used to extract the target compound from the obtained solid product; methanol was then removed to obtain the target compound. The reaction yield was almost 100%.

The following Table 1 shows the results of the aforementioned manufacturing method used under different conditions in terms of the kind of the solvent, the amount (in equivalents) of sodium periodate, and the presence/absence of the ruthenium trichloride.

"Test Numbers 1 and 2"

When ion-exchanged water was used for the reaction solvent, sodium periodate was used for the oxidation agent, and ruthenium trichloride was not used, the target chemical compound was not obtained.

"Test Number 3"

When a mixed solvent of ion-exchanged water and acetonitrile was used for the reaction solvent, ruthenium trichloride was used for the oxidation agent, and sodium periodate was not used, the target chemical compound was not obtained.

"Test Numbers 4 and 5"

When a mixed solvent of ion-exchanged water and acetonitrile was used for the reaction solvent, sodium periodate was used for the oxidation agent, and ruthenium trichloride was added, the target chemical compound was not obtained when the amount of sodium periodate was 1 equivalent. When the amount of sodium periodate was 2 equivalents, the target chemical compound was partially obtained but not sufficiently.

"Test Number 6"

When a mixed solvent of ion-exchanged water and acetonitrile was used for the reaction solvent, ruthenium trichloride was added, and the amount of sodium periodate was 3 equivalents, the target chemical compound was obtained with a yield of 75%. The obtained compound can be recrystallized from a methanol solution at rest or by adding acetonitrile to obtain a higher purity target compound.

"Test Numbers 7 and 8"

When a mixed solvent of ion-exchanged water and acetonitrile was used for the reaction solvent, ruthenium trichloride was added, and the amount of sodium periodate was 4 equivalents, the target chemical compound was obtained with a yield of 100%. The target chemical compound was also obtained with a yield of 100% when the reaction solvent was ion-exchanged water. The obtained compound can be recrystallized from a methanol solution at rest or by adding acetonitrile to obtain a higher purity target compound.

"Test numbers 9 and 10: The Present Invention"

When the reaction time of test number 8 was shortened to 1 hour, the chemical compound was obtained with a yield of 80%. On the other hand, when the reaction time of test number 7 was shortened to 1 hour, the target chemical compound was obtained with a yield of 100%. The obtained compound can be recrystallized from a methanol solution at rest or by adding acetonitrile to obtain a higher purity target compound.

"Manufacturing Method 3: A Manufacturing Method Using Permanganate (claim 4)"

1.0 g of glycerophosphorylcholine was dissolved in 20 ml of water and 1.85 g of potassium permanganate was added, followed by 3 hours of heating and stirring at 60° C. The reaction solution was neutralized with hydrochloric acid, the solvent was removed by means of pressure reduction, and the desired product was extracted using methanol and dried under a reduced pressure to obtain the target compound. The reaction yield was 82%.

"Example of a Surface Treatment Agent"

A quartz substrate was treated with plasma in the presence of hydrogen and nitrogen to obtain a quartz substrate having amino groups on the surface. This quartz substrate was immersed in water, to which compound (1) was added, and N-ethyl-N'-3-dimethylaminopropylcarbodiimide and N-hydroxysuccineimide were added, followed by 5 hours of stirring at room temperature. The quartz substrate was rinsed with water to obtain a quartz substrate whose surface was modified with phosphorylcholine groups.

INDUSTRIAL APPLICABILITY

The phosphorylcholine group-containing chemical compound of the present invention is a useful new compound as a surface treatment agent or a source material for a surface treatment agent for materials such as plastics, metal, and glass.

The surface modifier consisting of the compound of the present invention can give biocompatibility, moisture retaining properties, hydrophilicity, and other various useful functions to objects.

The manufacturing method of the present invention is a method using a one-step reaction with a water based solvent; the reaction proceeds quantitatively and the yield is very high. Furthermore, the purification process is simple and therefore the industrial utility value is very high.

The invention claimed is:

1. A method for manufacturing a phosphorylcholine group-containing chemical compound, represented by the following formula (1) or (3):

$$(CH_3)_3N^+CH_2CH_2PO_4^-CH_2COOH \qquad (1)$$

$$((CH_3)_3N^+CH_2CH_2PO_4^-CH_2COO^{31})_n M^{n+} \qquad (3)$$

TABLE 1

| | | Test number | | | | | | | | | |
|---|---|---|---|---|---|---|---|---|---|---|---|
| | | 1 | 2 | 3 | 4 | 5 | 6 | 7 | 8 | 9 | 10 |
| Reaction solvent | Ion-exchanged water | ○ | ○ | ○ | ○ | ○ | ○ | ○ | ○ | ○ | ○ |
| | Acetonitrile | — | — | ○ | ○ | ○ | ○ | ○ | — | — | ○ |
| | Glycerophosphorylcholine | ○ | ○ | ○ | ○ | ○ | ○ | ○ | ○ | ○ | ○ |
| Sodium periodate | Equivalents | 1 | 4 | — | 1 | 2 | 3 | 4 | 4 | 4 | 4 |
| | Ruthenium trichloride | — | — | ○ | ○ | ○ | ○ | ○ | ○ | ○ | ○ |
| | Reaction time | 2 h | 2 h | 2 h | 2 h | 2 h | 2 h | 2 h | 2 h | 1 h | 1 h |
| | Results | X | X | X | X | Produced a small amount | Produced | Produced | Produced | Produced | Produced | wherein M denotes a cation selected from the group consisting of alkali metal ions, alkali earth metal ions, and ammonium ion, and n denotes the valency of the cation, said method comprising:

reacting 1 part glycerophosphorylcholine with 3 or more parts periodic acid and/or periodate, and a trivalent ruthenium compound, in an aqueous solution.

2. A method for manufacturing a phosphorylcholine group-containing chemical compound represented by the following formula (1) or (3):

$$(CH_3)_3N^+CH_2CH_2PO_4^-CH_2COOH \quad (1)$$

$$((CH_3)_3N^+CH_2CH_2PO_4^-CH_2COO^{3-})_n M^{n+} \quad (3)$$

wherein M denotes a cation selected from the group consisting of alkali metal ions, alkali earth metal ions, and ammonium ion, and n denotes the valency of the cation, said method comprising:

reacting 1 part glycerophosphorylcholine with 3 or more parts periodic acid and/or periodate, and a diivalent ruthenium compound, in an aqueous solution.

3. A method for manufacturing a phosphorylcholine group-containing chemical compound represented by the following formula (1) or (3):

$$(CH_3)_3N^+CH_2CH_2PO_4^-CH_2COOH \quad (1)$$

$$((CH_3)_3N^+CH_2CH_2PO_4^-CH_2COO^{3-})_n M^{n+} \quad (3)$$

wherein M denotes a cation selected from the group consisting of alkali metal ions, alkali earth metal ions, and ammonium ion, and n denotes the valency of the cation, said method comprising:

reacting glycerophosphorylcholine, and permanganic acid and/or permanganate in an aqueous solution.

* * * * *